United States Patent
Alper et al.

(10) Patent No.: US 6,169,179 B1
(45) Date of Patent: *Jan. 2, 2001

(54) METHOD FOR MANUFACTURING (3S,4R)-4-[(R)-1'-FORMYLETHYL]AZETIDIN-2-ONE DERIVATIVES

(75) Inventors: Howard Alper, Ottawa (CA); Takao Saito; Takashi Miura, both of Hiratsuka (JP)

(73) Assignee: Takasago International Corporation, Tokyo (JP)

(*) Notice: Under 35 U.S.C. 154(b), the term of this patent shall be extended for 0 days.

(21) Appl. No.: 09/329,335

(22) Filed: Jun. 10, 1999

(30) Foreign Application Priority Data

Jul. 13, 1998 (JP) .................................................. 10-197204

(51) Int. Cl.[7] .............................. C07D 205/00; C07F 9/02
(52) U.S. Cl. .................................. 540/200; 568/8; 568/10; 568/13; 568/16; 568/17
(58) Field of Search .................................. 568/8, 13, 16, 568/17, 10; 540/200

(56) References Cited

U.S. PATENT DOCUMENTS 5,824,822 * 10/1998 Saito et al. .............................. 568/10

FOREIGN PATENT DOCUMENTS 6-263777 9/1994 (JP) .
6-316560 11/1994 (JP) .

OTHER PUBLICATIONS

Charles F. Hobbs, et al., "Asymmetric Hydroformylation of Vinyl Acetate with DIOP–Type Ligands", J.Org. Chem. vol. 46, 1981, pp. 4422–4427.

Serafino Gladiali, et al., "Completely Regioselective Hydroformylation of Methyl N–Acetamidoacrylate by Chiral Rhodium Phosphine Catalysts.", Tetrahedron: Asymmetry, vol. 1, No. 10, 1990, pp. 693–696.

Nozomu Sakai, et al., "Asymmetric Hydroformylation of Vinyl Acetate By Use of Chiral Bis(triarylphosphite)–Rhodium(I) Complexes", Tetrahedron:Asymmetry, vol. 3, No. 5, 1992, pp. 583–586.

Nozomu Sakai, et al., "Highly Enantioselective Hydroformylation of Olefins Catalyzed by New Phosphinephosphite–Rh(I) Complexes", J. Am. Chem. Soc., vol 115, 1993, pp. 7033–7034.

Teruyuki Hayashi, et al., "Catalytic Asymmetric Hydroformylation by the Use of Rhodium–complexes of Chiral Bidentate Phosphorus Ligands Bearing Saturated Ring Skeletons", Bulletin of the Chemical Society of Japan, vol. 52 (9), 1979, pp. 2605–2608.

* cited by examiner

Primary Examiner—Sreeni Padmanabhan
(74) Attorney, Agent, or Firm—Oblon, Spivak, McClelland, Maier & Neustadt, P.C.

(57) ABSTRACT

A method for manufacturing (3S,4R)-4-[(R)-1'-formylethyl]azetidin-2-one derivatives represented by formula (3) wherein $R^1$ represents a hydrogen atom or a protective group, through asymmetric hydroformylation of 4-vinylazetidin-2-one represented by formula (1) wherein $R^1$ has the same meaning as described above; in the presence of a rhodium complex and a (2S,4S)-diphosphine compound represented by formula (2) wherein $R^2$ represents a phenyl group which may be substituted with 1–5 substituent(s) selected from a lower alkyl group, a lower alkoxy group, and a halogen atom.

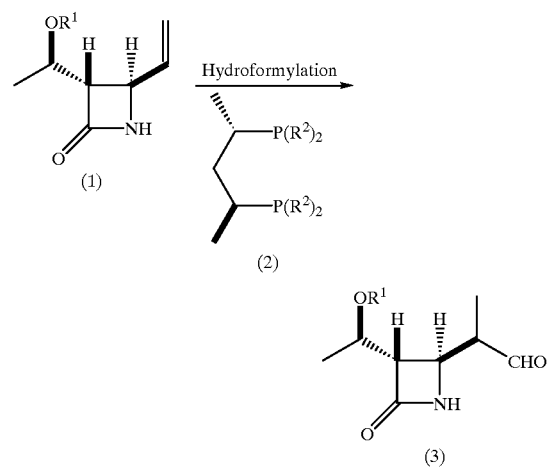

By use of both an inexpensive optically active diphosphine compound and a rhodium complex as catalysts, intermediate compounds important for carbapenem antibiotics can be manufactured with high selectivity and efficiency.

2 Claims, No Drawings

METHOD FOR MANUFACTURING (3S,4R)-4-[(R)-1'-FORMYLETHYL]AZETIDIN-2-ONE DERIVATIVES

BACKGROUND OF THE INVENTION

1. Field of the Invention

The present invention relates to a method for manufacturing (3S,4R)-4-[(R)-1'-formylethyl]azetidin-2-one derivatives—which are useful as intermediates for synthesis of carbapenem antibiotics—through asymmetric hydroformylation by use of both an optically active diphosphine compound and a rhodium complex as catalysts.

2. Description of the Related Art

In recent years, a number of metal complexes have been used in practice as catalysts for organic synthesis. Since noble metal complexes are stable and easy to handle, there have been conducted numerous synthesis studies have been conducted using such complexes as catalysts, regardless of their high prices. Thus, noble metal complexes have facilitated organic synthesis reactions which were believed to be impossible to carry out by conventional methods.

In particular, complexes of a transition metal such as rhodium or ruthenium and having an optically active diphosphine ligand are known as excellent catalysts for asymmetric synthesis, and a variety of phosphine compounds having a characteristic structure have been developed (edited by The Chemical Society of Japan, *Kagaku Sosetsu* 32 "Chemistry of Organometallics," pp. 237–238, 1982).

Asymmetric hydroformylation using a transition metal-optically active phosphine complex is one class of such reactions; e.g., reaction by use of a rhodium complex having an optically active 2,3-o-diisopropylidene-2,3-dihydroxy-1,4-bis(diphenylphosphino)-butane (hereinafter referred to as "DIOP") ligand (Journal of Organic Chemistry, vol. 46, page 4422 (1981)); reaction by use of a rhodium complex having an optically active diphosphine (e.g., DIOP) ligand (Bulletin of Chemical Society of Japan, vol. 52, page 2605 (1976)); and a catalytic asymmetric hydroformylation of methyl acetamideacrylate by use of a rhodium complex containing DIOP, etc. as a ligand (Tetrahedron Asymmetry, vol. 10, page 693 (1990)).

As a catalyst formed of a complex having an optically active tertiary phosphate ligand, Tetrahedron Asymmetry, vol. 3, page 583 (1992) describes bis(triaryl phosphite) having an optically active binaphthyl skeleton, as well as asymmetric hydroformylation of vinyl acetate making use of a rhodium complex containing the phosphate as a ligand.

Recently, it has also been reported that a ligand called BINAPHOS having an asymmetric structure, i.e., having a binaphthyl skeleton and no C2 symmetry, is useful for the asymmetric hydroformylation of olefins (J. Am. Chem. Soc., 115, 7033 (1993)).

Thus, a variety of catalysts for asymmetric synthesis are known. Nevertheless, there is still demand for development of a catalyst that meets requirements of high selectivity called for by some target compounds.

High selectivity is particularly needed in the field of pharmaceuticals. For example, there has been reported a method for manufacturing (3S,4R)-4-[(R)-1'-formylethyl] azetidin-2-one derivatives serving as important intermediates for carbapenem antibiotics which have been actively developed in recent years, through asymmetric hydroformylation of 4-vinylazetidin-2-one by use of an optically active phosphine-phosphite compound and a metal compound containing Rh, etc. as catalysts (Japanese Patent Application Laid-Open (kokai) No. 6-316,560).

A method has also been reported in which asymmetric hydroformylation of 4-vinylazetidin-2-one is performed by use of an optically active phosphine-phosphinite compound and a metal compound containing Rh, etc. as catalysts (Japanese Patent Application Laid-Open (kokai) No. 9-40,684).

PROBLEMS TO BE SOLVED BY THE INVENTION

In all the above-described methods, however, there is observed formation of a normal species (n-form:2'-formylethyl form) which is a by-product attributed to regioselectivity to a formyl group-bonding and simultaneous formation of an S-species (i.e., α-form) affecting the enantioselectivity in addition to an (R)-species (i.e., β-form), which is a target compound, attributed to configuration of a formyl group-bonding. Therefore, there has been demand for satisfying both regioselectivity and enantioselectivity, as well as the demand for obtaining a target compound in high yield.

In particular, there has been demand for a method for effectively manufacturing (3S,4R)-4-[(R)-1'-formylethyl] azetidin-2-one derivatives having a methyl group at the β-position, which are of great value for use as important intermediates for carbapenem antibiotics, with high regioselectivity and enantioselectivity.

SUMMARY OF THE INVENTION

The present inventors have conducted earnest studies to solve the above problems, and found that (3S,4R)-4-[(R)-1'-formylethyl]azetidin-2-one derivatives having a methyl group at the β-position of the present invention are effectively manufactured through asymmetric hydroformylation by use of both an inexpensive and easily available optically active diphosphine compound and a rhodium complex as catalysts. The present invention was accomplished based on this finding.

Accordingly, the present invention provides a method for manufacturing (3S,4R)-4-[(R)-1'-formylethyl]azetidin-2-one derivatives represented by formula (3):

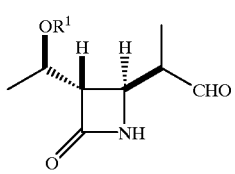

(3)

wherein $R^1$ represents a hydrogen atom or a protective group for a hydroxyl group; through asymmetric hydroformylation of 4-vinylazetidin-2-one represented by formula (1):

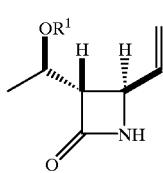

(1)

wherein R¹ has the same meaning as described above; in the presence of a rhodium complex and a (2S,4S)-diphosphine compound represented by formula (2):

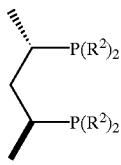

(2)

wherein R² represents a phenyl group which may be substituted with 1–5 substituent(s) selected from a lower alkyl group, a lower alkoxy group, and a halogen atom.

DETAILED DESCRIPTION OF THE PREFERRED EMBODIMENTS

Hereafter, the present invention will be described in detail.

The 4-vinylazetidin-2-one (formula (1)) used as starting materials in the present invention are conventionally known compounds, which may be synthesized through, for example, a method described in Liebig Ann. Chem., 539–560 (1974).

Specifically, a 4-acetoxyazetidinon-2-one derivative (formula (4)) is subjected to reaction with sodium benzenesulfinate, sodium p-toluenesulfinate, or the corresponding potassium salt or lithium salt in a soluble solvent such as acetone-water, methanol, or water-methanol to thereby derive to a compound represented by formula (5). Subsequently, this compound is reacted with an organic vinyl compound—for example, a vinylating agent such as vinyl magnesium chloride, vinyl magnesium bromide, vinyl magnesium iodide, divinyl magnesium, vinyl lithium, vinyl zinc chloride, or divinyl zinc—to thereby obtain 4-vinylazetidin-2-one (formula (1)):

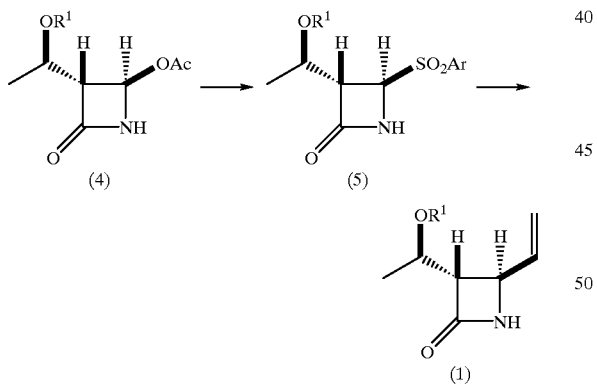

wherein R¹ has the same meaning as described above; Ac represents an acetyl group; and Ar represents a phenyl group which may be substituted with a halogen atom, a lower alkyl group, etc.

The substituent R¹ in 4-vinylazetidin-2-one (formula (1)) represents a hydrogen atom or a protective group for a hydroxyl group, and as the protective group for a hydroxyl group there may be used typical protective groups, i.e., a protective group which may be converted to a hydroxyl group through hydrolysis or hydrogenation used. Examples include organic silyl groups, an acyl group, and aralkyl groups. Specific examples include tri-lower alkylsilyl groups, diphenyl-lower alkylsilyl groups, a triphenylsilyl group, lower alkylcarbonyl groups, a benzyl group, and a benzoyl group. Preferred examples include tri-lower alkylsilyl groups and diphenyl-lower alkylsilyl groups.

Of these protective groups for a hydroxyl group, there is preferred a group substituted with a linear or branched alkyl group having 1–6 carbon atom(s) as the lower alkyl substituent. Examples of the tri-lower alkylsilyl groups include a tert-butyldimethylsilyl group, a dimethyltexylsilyl group, a triethylsilyl group, a truisopropylsilyl group, and a trimethylsilyl group, with a tert-butyldimethylsilyl group being particularly preferred. A tert-butyldiphenylsilyl group is preferred as the diphenyl-lower alkyl group.

(3S,4R)-4-[(R)-1'-Formylethyl]azetidin-2-one derivatives (formula (3)), which are the target compounds of the present invention, may be manufactured through asymmetric hydroformylation of the above-described 4-vinylazetidin-2-one (formula (1)) by use of an optically active diphosphine compound (formula (2)) and a rhodium compound as catalysts.

In accordance with the present invention, asymmetric hydroformylation of 4-vinylazetidin-2-one (formula (1)) in the presence of an (S,S)-form of a diphosphine compound and a rhodium compound enables selective and effective manufacture of a product of β-form in particular among three possibly formed isomers of α-form, β-form, and n-form:

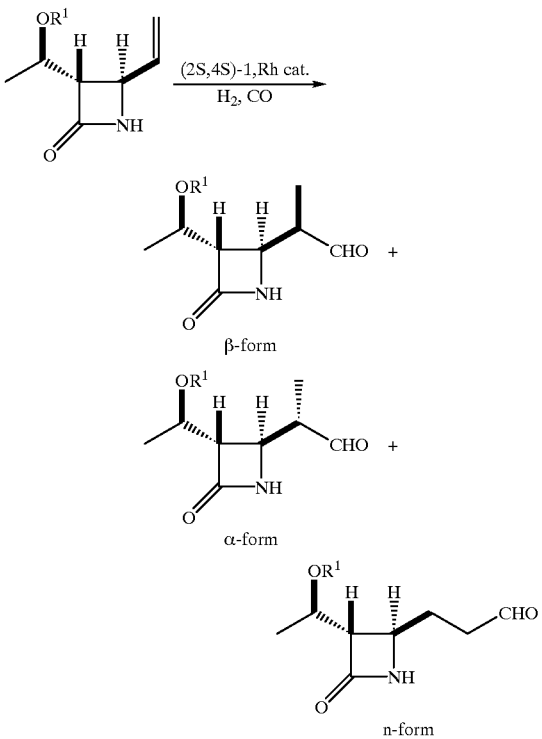

wherein R¹ has the same meaning as described above.

In the diphosphine compounds used as catalysts in the present invention, R² in formula (2) represents a phenyl group which may be substituted with 1–5 substituent(s) selected from a lower alkyl group, a lower alkoxy group, and a halogen atom, and the preferred number of these substituents is 0–3.

Examples of the lower alkyl group substituents to a phenyl group include a linear or branched alkyl group having 1–4 carbon atom(s) such as a methyl group, an ethyl group, a propyl group, an isopropyl group, an n-butyl group, a sec-butyl group, an isobutyl group, or a tert-butyl group. Preferred examples of the phenyl group substituted with the lower alkyl group(s) include an o-tolyl group, an m-tolyl group, a p-tolyl group, a 3,5-dimethylphenyl group, a mesityl group, a 3,5-di(tert-butyl)phenyl group, and a 3,5-diethylphenyl group.

Examples of the lower alkoxy group substituents to a phenyl group include a linear or branched alkoxy group having 1–4 carbon atom(s) such as a methoxy group, an ethoxy group, a propyloxy group, an isopropyloxy group, and a tert-butoxy group. Preferred examples of the phenyl group substituted with the lower alkoxy group(s) include a p-methoxyphenyl group, an m-methoxyphenyl group, and a 3,5-dimethoxyphenyl group.

Furthermore, examples of the halogen atom substituents to a phenyl group include a fluorine atom, a chlorine atom, a bromine atom, and an iodine atom. Preferred examples of the phenyl group substituted with the halogen atom(s) include a p-fluorophenyl group, a 3,5-difluorophenyl group, a p-chlorophenyl group, a 3,5-dichlorophenyl group, a p-bromophenyl group, and a 3,5-dibromophenyl group.

Examples of the diphosphine compounds used as ligands in the asymmetric hydroformylation of the present invention include compounds as described above; however, use of a diphosphine compound having a configuration of (S,S) is an essential condition for obtaining (3S,4R)-4-[(R)-1'-formylethyl]azetidin-2-one derivatives (formula (3)), which are the target compounds. A (2S,4S)-form of the diphosphine compound must be used in order to obtain a target compound of the present invention. These diphosphine compounds may typically be used in an amount of 0.0005–10 mol %, preferably 0.001–5 mol %, with respect to 4-vinylazetidin-2-one (formula (1)) serving as a substrate.

With regard to a rhodium complex serving as the other catalyst component, a zwitterionic complex is preferred, and specific examples include a compound represented by formula (4):

$$Rh^{\oplus}(I)(L)(\eta^6-C_6H_5B^{\ominus}Ph_3) \qquad (4)$$

wherein L represents 1,5-cyclooctadiene (hereinafter referred to as "COD") or norbornadiene (hereinafter referred to as "NBD"), Ph represents a phenyl group, and Rh means Rh(I).

Examples of the rhodium complexes include $Rh^{\oplus}(COD)(\eta^6-C_6H_5B^{\ominus}h_3)$ and $Rh^{\oplus}(NBD)(\eta^6-C_6H_5B^{\ominus}Ph_3)$, and the latter complex is preferred. The rhodium complex may be used in a ¼ mole amount to an equimole amount based on the optically active diphosphine compound used, and is preferably used in a ⅓ to ½ mole amount.

No particular limitation is imposed on the solvents used in the present invention, and any solvent may be used so long as it effects reaction. Hydrocarbons are particularly preferred. Specific examples include n-hexane, n-heptane, n-octane, isooctane, nonane, decane, cyclohexane, cyclopentane, benzene, toluene, xylene, and mesitylene. In addition to these solvents, examples include ethers such as diisopropyl ether, dibutyl ether, tetrahydrofuran, dimethoxyethane, or diethylene glycol dimethyl ether; ketones such as acetone or methyl ethyl ketone; and esters such as ethyl acetate, butyl butyrate, or butyl benzoate. These solvents may be used singly or in combination of two or more species.

The reaction temperature of hydroformylation of the present invention is preferably low in view of thermal stability of formed aldehyde, although it is preferably high in view of the reaction rate. The temperature is typically −20–250° C., preferably 10–120° C. The reaction may be carried out for a reaction time of 1–48 hours, and is preferably carried out for 6–30 hours.

The asymmetric hydroformylation of the present invention is conducted in the presence of carbon monoxide and hydrogen in a similar manner as that for typical hydroformylation. In this case, the reaction may be carried out under the reaction pressure of 5–200 kg/cm², preferably 20–150 kg/cm² and the mixing mole ratio of carbon monoxide to hydrogen, carbon monoxide/hydrogen, is 10–0.1, preferably 4–0.25. The gas system may be diluted with another reaction-inert gas so long as the mixing mole ratio of carbon monoxide to hydrogen is maintained within the given range. For example, methane, nitrogen, argon, helium, carbon dioxide, etc. may be used singly or in combination of two or more species.

The asymmetric hydroformylation of the present invention provides remarkable lowering of formation of the n-form, which has been a problem in conventional methods, and enables synthesis of the β-form, which is the target compound, with selectivity as high as about 84% based on the β-form/α-form/n-form.

The thus-obtained (3S,4R)-4-[(R)-1'-formylethyl]-azetidin-2-one derivatives (formula (3)), which are target compounds of the present invention, easily undergo conversion of a formyl group to a carboxyl group, through customary oxidation, e.g., Jones oxidation, and are finally converted to useful intermediates derived to carbapenem antibiotics.

EXAMPLE

The present invention will next be described in detail by way of examples, which should not be construed as limiting the invention thereto.

The apparatus used for measurement of properties in each of the Examples are as follows.

* Nuclear magnetic resonance spectra (NMR) AM-400 (Bruker Co., 400 MHz)
  Internal standards
  $^1$H-NMR: tetramethylsilane
  $^{31}$P-NMR: 85% phosphoric acid
* High performance liquid chromatography (HPLC) Hitachi-L-6000 (Hitachi, Ltd.)

Example 1

Synthesis of (3S,4R)-3-((R)-1-tert-butyldimethylsilyloxy)ethyl-4-((R -1'-formylethyl)-azetidin-2-one $Rh^{\oplus}(NBD)(\eta^6-C_6H_5B^{\ominus}Ph_3)$ (5.1 mg, 0.01 mmol), (2S, 4S)-bis(diphenyl)phosphinopentane (8.8 mg, 0.02 mmol), and (1S,3S,4R)-vinylazetidin-2-one (127.7 mg, 0.5 mmol) were placed in a 45 ml-autoclave, the inside of which was purged with nitrogen. To the mixture was added benzene (5 ml) and a mixture gas containing carbon monoxide/hydrogen=1/1 was fed at 50 kg/cm² to apply pressure. The mixture was allowed to react for 24 hours with heating at 76° C. in an oil bath and stirring. Then, the reaction mixture was allowed to stand and cool to ambient temperature, and excess carbon monoxide and hydrogen were removed.

The obtained reaction mixture was subjected to HPLC analysis to prove that selection ratios in relation to (3S,4R)-3-((R)-1-tert-butyldimethylsilyloxy)ethyl-4-((R)-1'-formylethyl)-azetidin-2-one (β-form), (3S,4R)-3-((R)-1-tert-butyldimethylsilyloxy)ethyl-4-((S)-1'-formylethyl)-azetidin-2-one (α-form), and (3S,4R)-3-((R)-1-tert-butyldimethylsilyloxy)ethyl-4-(formylethyl)-azetidin-2-one (n-form) were β-form/α-form=88/12 and β-form+α-form/n-form=96/4, i.e., β-form/α-form/n-form=84.5/11.5/4.0.

The ratios of β-form/α-form and β-form+α-form/n-form were determined through integral ratios attributed to aldehyde proton in $^1$H-NMR and HPLC (Cosmosil 5C18-MS (product of Nakarai Tesuku Co.), eluant: acetonitrile/water=65/35, flow speed: 0.5 ml/min, detector: Shodex RI SE-51).

(β-form)
$^1$H-NMR (400 MHz, CDCl$_3$,δ) 0.07 ( s, 3H), 0.08 ( s, 3H), 0.88 (s, 9H) 1.22 (d, J=7.3 Hz, 3H), 1.24 (d, J=6.3 Hz) 2.68 (m, 1H), 3.94 (dd, J=5.4, 2.4 Hz, 1H) 4.20 (m, 1H), 5.98 (s, 1H), 9.81 (d, J=1.1 Hz, 1H)

Example 2

The procedure of Example 1 was performed using (2S, 4S)-bis(p-tolyl)phosphinopentane as the phosphine compound, to thereby obtain a target compound. The obtained target compound was subjected to HPLC analysis to prove β-form/α-form=86/14 and β-form+α-form/n-form=95/5, i.e., β-form/α-form/n-form=81.7/13.3/5.

Examples 3 and 4

The procedure of Example 1 was performed using solvents specified in Table 1 below, to thereby obtain target compounds.

Thus the formyl form as the target compounds were obtained at formation ratios shown in Table 1.

TABLE 1

| Example | Solvent | β/α | β + α/n | β/α/n |
|---|---|---|---|---|
| 3 | Cyclohexane | 90/10 | 88/12 | 79.2/8.8/12 |
| 4 | Toluene | 89/11 | 93/7 | 82.8/10.2/7 |

Example 5

The procedure of Example 1 was performed employing pressures of carbon monoxide and hydrogen specified in Table 2 below, to thereby obtain a target compound.

Thus, formyl form as the target compound was obtained at formation ratios shown in Table 2.

TABLE 2

| Example | Pressure | β/α | β + α/n | β/α/n |
|---|---|---|---|---|
| 5 | 100 kg/cm$^2$ | 77/23 | 91/9 | 70.1/20.9/9 |

Examples 6 and 7

The procedure of Example 1 was performed employing temperature specified in Table 3 below, to thereby obtain target compounds.

Thus, formyl form as the target compounds were obtained at formation ratios shown in Table 3.

TABLE 3

| Example | Temp. | β/α | β + α/n | β/α/n |
|---|---|---|---|---|
| 6 | 45° C. | 87/13 | 97/3 | 84.4/23.6/3 |
| 7 | 96° C. | 85/15 | 88/12 | 74.8/10.2/12 |

As described above, in the present invention, there can be manufactured (3S,4R)-4-[(R)-1'-formylethyl]azetidin-2-one derivatives, which are important intermediates for carbapenem antibiotics, with high selectivity and efficiency through asymmetric hydroformylation of 4-vinylazetidin-2-one by use of both an inexpensive optically active diphosphine compound and a rhodium complex as catalysts.

What is claimed is:

1. A method for manufacturing (3S,4R)-4-[(R)-1'-formylethyl]azetidin-2-one derivatives represented by formula (3):

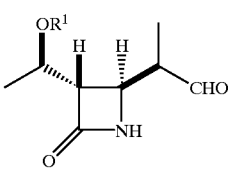

(3)

wherein R$^1$ represents a hydrogen atom or a protective group for a hydroxyl group; through asymmetric hydroformylation of 4-vinylazetidin-2-one represented by formula (1):

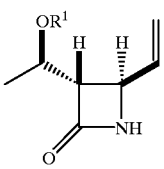

(1)

wherein R$^1$ has the same meaning as described above; in the presence of a rhodium complex and a (2S,4S)-diphosphine compound represented by formula (2):

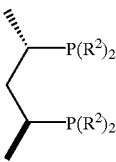

(2)

wherein R$^2$ represents a phenyl group which may be substituted with 1–5 substituent(s) selected from a lower alkyl group, a lower alkoxy group, and a halogen atom.

2. The method for manufacturing (3S,4R)-4-[(R)-1'-formylethyl]azetidin-2-one derivatives according to claim 1, wherein the rhodium complex is represented by formula (4):

$$Rh^{\oplus}(I)(L)(\eta^6-C_6H_5B^{\ominus}Ph_3) \qquad (4)$$

wherein L represents 1,5-cyclooctadiene or norbornadiene and Ph represents a phenyl group.

* * * * *